United States Patent
Bai et al.

(10) Patent No.: US 8,932,455 B2
(45) Date of Patent: Jan. 13, 2015

(54) INTERSTITIAL METAL HYDRIDE CATALYST SYSTEMS AND ASSOCIATED PROCESSES

(71) Applicants: Chuansheng Bai, Phillipsburg, NJ (US); Adrienne J. Thornburg, Allentown, PA (US); Heather A. Elsen, Bethlehem, PA (US); Jean W. Beeckman, Columbia, MD (US); William G. Borghard, Haddon Heights, NJ (US)

(72) Inventors: Chuansheng Bai, Phillipsburg, NJ (US); Adrienne J. Thornburg, Allentown, PA (US); Heather A. Elsen, Bethlehem, PA (US); Jean W. Beeckman, Columbia, MD (US); William G. Borghard, Haddon Heights, NJ (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 14/071,738

(22) Filed: Nov. 5, 2013

(65) Prior Publication Data
US 2014/0081060 A1    Mar. 20, 2014

Related U.S. Application Data

(62) Division of application No. 12/942,271, filed on Nov. 9, 2010, now Pat. No. 8,598,067.

(51) Int. Cl.
*C10G 47/02* (2006.01)
*C10G 45/04* (2006.01)
(Continued)

(52) U.S. Cl.
CPC .............. *C10G 47/14* (2013.01); *B01J 23/8877* (2013.01); *B01J 27/0515* (2013.01);
(Continued)

(58) Field of Classification Search
CPC ........ C10G 47/14; C10G 45/10; C10G 45/40; C10G 49/06; B01J 31/12; B01J 31/121
USPC ......... 208/22, 40, 112, 134, 143, 216 R, 217, 208/253, 251 H, 254 H; 502/102, 103, 113, 502/114; 585/240, 277
See application file for complete search history.

(56) References Cited

U.S. PATENT DOCUMENTS 2,881,131 A    4/1959 Kearby
3,736,265 A    5/1973 Suggitt
(Continued)

FOREIGN PATENT DOCUMENTS

EP    1708297 A1    10/2006
EP    1946837 A2    7/2008

OTHER PUBLICATIONS

Nicholas E. Leadbeater, Rashid M. Khan, "Microwave-Promoted Desulfurization of Heavy and Sulfur-Containing Crude Oil," Energy & Fuels (2008), 22(3), 1836-1839 Abstract.
(Continued)

*Primary Examiner* — Prem C Singh
*Assistant Examiner* — Brandi M Doyle
(74) *Attorney, Agent, or Firm* — Bruce M. Bordelon; Glenn T. Barrett; Chad A. Guice

(57) ABSTRACT

Exemplary embodiments of the present invention relate to the processing of hydrocarbon-containing feedstreams in the presence of an interstitial metal hydride containing catalyst comprising a surface, and a Group VI/Group VIII metal sulfide coated onto the surface of the interstitial metal hydride. The catalysts and processes of the present invention can improve overall hydrogenation, product conversion, as well as sulfur reduction in hydrocarbon feedstreams.

6 Claims, 4 Drawing Sheets

(51) Int. Cl.

| | | |
|---|---|---|
| *C10G 47/14* | (2006.01) | |
| *B01J 23/887* | (2006.01) | |
| *B01J 27/051* | (2006.01) | |
| *B01J 31/12* | (2006.01) | |
| *B01J 35/00* | (2006.01) | |
| *B01J 37/00* | (2006.01) | |
| *B01J 37/04* | (2006.01) | |
| *B01J 37/08* | (2006.01) | |
| *C10G 3/00* | (2006.01) | |
| *C10G 49/06* | (2006.01) | |
| *C07C 4/06* | (2006.01) | |
| *C07C 5/03* | (2006.01) | |
| *C07C 7/173* | (2006.01) | |
| *C10G 45/10* | (2006.01) | |
| *C10G 45/40* | (2006.01) | |

(52) U.S. Cl.
CPC ............. *B01J 31/121* (2013.01); *B01J 35/002* (2013.01); *B01J 37/0036* (2013.01); *B01J 37/04* (2013.01); *B01J 37/08* (2013.01); *C10G 3/50* (2013.01); *C10G 49/06* (2013.01); *C10G 3/46* (2013.01); *C10G 3/47* (2013.01); *C10G 3/48* (2013.01); *C07C 4/06* (2013.01); *C07C 5/03* (2013.01); *C07C 7/173* (2013.01); *C10G 45/10* (2013.01); *C10G 45/40* (2013.01); *B01J 2531/48* (2013.01); *B01J 2531/56* (2013.01); *C10G 2300/202* (2013.01); *C10G 2300/308* (2013.01)
USPC ........ 208/112; 208/134; 208/143; 208/216 R; 208/217; 208/251 H; 208/253; 208/254 H; 585/240

(56) References Cited

U.S. PATENT DOCUMENTS

| | | | |
|---|---|---|---|
| 3,758,614 | A | 9/1973 | Mertzweiller et al. |
| 4,025,606 | A | 5/1977 | Acres |
| 4,040,410 | A | 8/1977 | Libowitz |
| 4,120,763 | A | 10/1978 | Breda et al. |
| RE30,083 | E | 8/1979 | Reilly et al. |
| 4,279,722 | A | 7/1981 | Kirkbride |
| 4,302,436 | A | 11/1981 | Sirovich et al. |
| 4,492,769 | A | 1/1985 | Blanchard et al. |
| 4,545,879 | A | 10/1985 | Wan et al. |
| 4,556,551 | A | 12/1985 | Wallace et al. |
| 4,560,816 | A | 12/1985 | Davis, Jr. |
| 5,286,698 | A | 2/1994 | Carberry et al. |
| 5,332,705 | A | 7/1994 | Huang et al. |
| 5,525,435 | A | 6/1996 | Pourarian |
| 5,695,530 | A | 12/1997 | Hong et al. |
| 6,017,845 | A | 1/2000 | Ovalles et al. |
| 6,040,087 | A | 3/2000 | Kawakami |
| 6,165,643 | A | 12/2000 | Doyle et al. |
| 6,171,479 | B1 | 1/2001 | Ovalles et al. |
| 6,403,523 | B1 | 6/2002 | Cantrell et al. |
| 6,670,490 | B1 | 12/2003 | Campos et al. |
| 6,680,042 | B1 | 1/2004 | Schulz et al. |
| 7,157,401 | B2 | 1/2007 | Purta et al. |
| 7,387,712 | B2 | 6/2008 | Purta et al. |
| 7,455,927 | B2 | 11/2008 | DiSalvo, Jr. et al. |
| 7,601,329 | B2 | 10/2009 | Vajo et al. |
| 7,700,069 | B2 | 4/2010 | Stephens |
| 2002/0013221 | A1 | 1/2002 | Thompson et al. |
| 2002/0177735 | A1 | 11/2002 | Kanamori et al. |
| 2003/0073571 | A1 | 4/2003 | Heijden et al. |
| 2004/0074759 | A1 | 4/2004 | Purta et al. |
| 2004/0074760 | A1 | 4/2004 | Portnoff et al. |
| 2004/0077485 | A1 | 4/2004 | Purta et al. |
| 2005/0202965 | A1 | 9/2005 | Cavalcanti et al. |
| 2005/0274065 | A1 | 12/2005 | Portnoff et al. |
| 2006/0096893 | A1 | 5/2006 | De Almeida et al. |
| 2007/0087933 | A1 | 4/2007 | Purta et al. |
| 2007/0202335 | A1 | 8/2007 | Kubota |
| 2008/0233020 | A1 | 9/2008 | Purta et al. |
| 2008/0262114 | A1 | 10/2008 | Reynhout |
| 2008/0302703 | A1 | 12/2008 | Purta et al. |
| 2011/0119990 | A1 | 5/2011 | Venkataraman et al. |
| 2011/0119992 | A1 | 5/2011 | Pourarian et al. |
| 2012/0111768 | A1 | 5/2012 | Elsen |

OTHER PUBLICATIONS

L. K. Heung, G. G. Wicks, "Silica embedded metal hydrides," Journal of Alloys and Compounds 293-295 (1999) pp. 446-451.

Visintin, A. et al., "Electrochemical activation and electrocatalytic enhancement of a hyride-forming metal alloy modified with palladium, platinum and nickel", Electrochimica Acta, 2006, pp. 3658-3667, vol. 1.

INTERSTITIAL METAL HYDRIDE CATALYST SYSTEMS AND ASSOCIATED PROCESSES

CROSS REFERENCE TO RELATED APPLICATIONS

This application is a divisional application of U.S. patent application Ser. No. 12/942,271, filed on Nov. 9, 2010 now U.S. Pat. No. 8,598,607.

FIELD OF THE INVENTION

The present invention relates to catalysts for the processing of hydrocarbon-containing feedstreams. The catalysts include an interstitial metal hydride with a Group VI/Group VIII metal sulfide coated onto the surface of the interstitial metal hydride. The processes of the present invention use the interstitial metal hydride containing catalysts for improved overall hydrogenation, product conversion, and sulfur reduction in hydrocarbon feedstreams.

INTRODUCTION

As the demand for hydrocarbon-based fuels has risen, the need for improved processes for desulfurizing hydrocarbon feedstreams has increased, as well as the need for increasing the conversion of the heavy portions of these feedstreams into more valuable, lighter fuel products. These hydrocarbon feedstreams include, but are not limited to, whole and reduced petroleum crudes, shale oils, coal liquids, atmospheric and vacuum residua, asphaltenes, deasphalted oils, cycle oils, FCC tower bottoms, gas oils, including atmospheric and vacuum gas oils and coker gas oils, light to heavy distillates including raw virgin distillates, hydrocrackates, hydrotreated oils, dewaxed oils, slack waxes, raffinates, biofuels, and mixtures thereof.

Hydrocarbon streams boiling above 430° F. (220° C.) often contain considerable amounts of large multi-ring hydrocarbon molecules and/or conglomerated associations of large molecules containing a large portion of the sulfur, nitrogen and metals present in the hydrocarbon stream. A significant portion of the sulfur contained in these heavy oils is in the form of heteroatoms in polycyclic aromatic molecules, such as dibenzothiophenes, from which the sulfur is difficult to remove.

The high molecular weight, large multi-ring aromatic hydrocarbon molecules or associated heteroatom-containing (e.g., S, N, O) multi-ring hydrocarbon molecules in heavy oils are generally found in a solubility class of molecules termed as asphaltenes. A significant portion of the sulfur is contained within the structure of these asphaltenes or lower molecular weight polar molecules termed as "polars" or "resins". Due to the large aromatic structures of the asphaltenes, the sulfur can be refractory in nature and can be difficult to remove. In conventional refining processes, sulfur compounds are removed in refinement processes from various hydrocarbon streams by "cracking" the petroleum oils in the presence of a metal catalyst and hydrogen. These conventional refining processes for sulfur removal from hydrocarbon streams are known by such names as "hydrodesulfurization" processes or "hydrocracking" processes, and are well known in the industry.

In these processes, the sulfur atoms in the hydrocarbon streams are exposed or separated from the oil and are able to react with hydrogen which is then liberated from the process typically in the form of a hydrogen sulfide gas. In these processes, nitrogen and metals are also removed to some extent from the hydrocarbon streams (i.e., "denitrogenation" and "demetalization"). However, nitrogen and/or metals are sometimes targeted for removal by "pre-processing" the hydrocarbon streams and removing a portion of the nitrogen and/or metals (which may include some amount of reaction cracking and/or desulfurization) prior to contacting the primary hydrodesulfurization or hydrocracking catalysts. Additionally, in these hydrodesulfurization or hydrocracking processes, some of the larger hydrocarbon molecules are "cracked" into smaller hydrocarbon molecules. This is generally called "cracking" or "conversion" and is a significant part of many of these hydroprocessing processes as this converts heavier, low value petroleum streams, such as gas oils and resids, into higher value products such as transportation fuels, for example, gasolines, jet fuels, and diesels.

Alternatives to conventional hydroprocessing processes have been proposed in U.S. Pat. Nos. 7,157,401 and 7,387,712 to Purta et al. In these processes, petroleum oils are contacted with interstitial metal hydride ("iMeH") catalysts under mild conditions for hydrogenation of molecules. In particular, these patents disclose three specific compositions of iMeHs: Cat 100 (or "$AT_5$ type"), CAT 200 (or "$A_2T_{14}B$ type") and CAT 300 (or "$A_2T$ type"). It is shown in these patents that the iMeH catalysts show improved hydrogenation activities in the presence of microwaves under mild processing conditions (200° C. at 50 psig).

While the iMeH systems described above are useful as hydroprocessing catalysts, there remains a need in the art to further improve the activities of iMeH catalysts to make the processes of heavy hydrocarbon conversion and upgrading more economically attractive and feasible. In particular, catalysts with higher activities and improved long-term stabilities are desirable.

BRIEF DESCRIPTION OF THE INVENTION

Exemplary embodiments of the current invention relate to catalysts and processes for hydroprocessing a hydrocarbon-containing feedstream to produce a product stream with improved product qualities.

In one aspect, the invention features a catalyst comprising an interstitial metal hydride ("iMeH") having a surface, and a Group VI/Group VIII metal sulfide coated on the surface of the iMeH.

In certain embodiments of the catalyst of the present invention, the iMeH has a compositional formula of $A_{1-x}M_x T_{5-y-z}B_yC_z$, wherein:
   A=Mm (mischmetal); T=Ni; M=La, Pr, Nd or Ce; B=Co; C=Mn, Al or Cr; and
   x=0.0 to 1.0; y=0.0 to 2.5; and z=0.0 to 0.5.

In other embodiments of the catalyst of the present invention, the iMeH has a compositional formula of $A_{2-x}M_x T_{14-y}C_yD_zB$, wherein:
   A=Nd or Pr; T=Fe; M=La, Pr, Nd or Ce; B=Boron; C=Co; D=Cr, Ni or Mn; and
   x=0.0 to 2.0; y=0.0 to 14; and z=0.0 to 3.0.

In some embodiments of the catalyst of the present invention, the iMeH has a compositional formula of $A_{2-x}M_xT_{1-y}B_y$, wherein:
   A=Mg; T=Ni or Cu; M=La; B=Fe or Co; and
   x=0.0 to 0.5; and y=0.0 to 0.5.

In certain embodiments of the catalyst of the present invention, the iMeH has a compositional formula of $A_{1-x}B_x T_{(2-y)\pm d1}C_{y\pm d2}$, wherein:

A=Nd or Zr; B=at least one of La, Ce, Pr, Gd, Tb, Dy, Er, Ho, Ti and Hf; T=at least one of Fe and V; C=at least one of Cr, Mn, Fe, Co, Ni and Cu; and x=0.0 to 1.0; and y=0.0 to 2.0; and $d_1$=0.00 to 0.2; and $d_2$=0.00 to 0.2.

In some embodiments of the catalyst of the present invention, the Group VI metal is selected from Mo and W, and the Group VIII metal is selected from Fe, Co, Ni, Pd, and Pt. In exemplary embodiments, the Group VI metal is Mo and the Group VIII metal is selected from Co and Ni.

In some embodiments of the catalyst of the present invention, the Group VI/Group VIII metal sulfide is coated on the surface of the interstitial metal hydride by in-situ decomposition of at least one Group VI metal salt and at least one Group VIII metal salt. In some embodiments, the Group VI metal salt is selected from Mo and W salts. In some embodiments, the Group VIII metal salt is selected from Fe, Co, Ni, Pd, and Pt salts. In an exemplary embodiment, the Group VI metal salt is a Mo salt and the Group VIII metal salt is selected from Co and Ni salts.

In some embodiments of the catalyst of the present invention, the interstitial metal hydride and the Group VI/Group VIII metal sulfide are present in a ratio of about 20:80 by weight to about 80:20 by weight (e.g., about 65:35 by weight to about 35:65 by weight, or about 50:50 by weight).

In some embodiments of the catalyst of the present invention, the activity of the catalyst is greater than the sum of the activity of the same weight % of interstitial metal hydride and the activity the same weight % of Group VI/Group VIII metal sulfide. This "synergy" or synergistic effect can be calculated and compared against the base components to determine the amount of unexpected improved activity experienced by the particular combination(s). Further information concerning calculating the synergy, as well as the synergistic effects experienced by one of the embodiments herein, is further illustrated in Example 6 herein and associated FIG. 3.

In another aspect, the present invention features a method of making an interstitial metal hydride having a surface, and a Group VI/Group VIII metal sulfide coated on the surface of the iMeH, comprising contacting an interstitial metal hydride having a surface with a Group VI metal salt and a Group VIII metal salt, under conditions sufficient to form a Group VI/Group VIII metal sulfide, thereby coating the surface of the iMeH with the Group VI/Group VIII metal sulfide.

In another aspect, the present invention provides a process for upgrading a hydrocarbon feedstream comprising contacting a hydrocarbon feedstream with a catalyst comprising an iMeH having a surface, and a Group VI/Group VIII metal sulfide coated on the surface of the iMeH, in the presence of hydrogen to yield an upgraded hydrocarbon product stream.

In another aspect, the present invention features a catalyst comprising an interstitial metal hydride having a surface, and a Group VI/Group VIII metal sulfide coated on the surface of the interstitial metal hydride, wherein the activity of the catalyst is greater than the sum of the activity of the interstitial metal hydride alone and the activity Group VI/Group VIII metal sulfide alone.

DETAILED DESCRIPTION OF THE INVENTION

Figure 1:
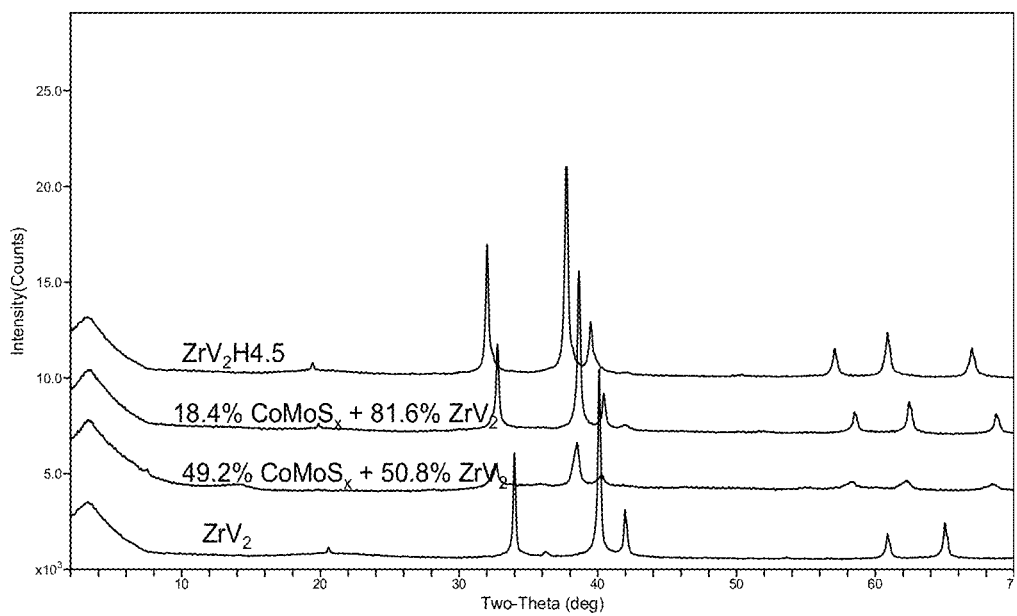
FIG. 1 depicts X-ray powder diffraction patterns of two catalysts, 18.4% $CoMoS_x$+81.6% $ZrV_2$ and 49.2% $CoMoS_x$+ 50.8% $ZrV_2$, as well as the reference samples of a $ZrV_2$ alloy and $ZrV_2H_{4.5}$ metal hydrides.

Exemplary embodiments of the current invention relate to catalysts and processes for hydroprocessing a hydrocarbon-containing feedstream to produce a product stream with improved product qualities, by using an interstitial metal hydride ("iMeH") catalyst with a Group VI/Group VIII metal sulfide coated on its surface. These new catalyst systems possess significant improvements in hydroprocessing of hydrocarbon feedstreams. Specifically, a catalyst featuring an iMeH with a Group VI/Group VIII metal sulfide coated on its surface may utilize monatomic hydrogen more effectively, providing catalysts with improved hydrogenation activities and increased long-term stabilities.

DEFINITIONS

As used herein, "improved product qualities" include, but are not limited, to increased hydrogenation (or increased hydrogen content by weight), lower average boiling point conversion (or "cracking"), higher API gravity, reduced viscosity, and lower levels of sulfur, nitrogen, and metals.

The terms "hydrocarbon-containing stream", "hydrocarbon stream" or "hydrocarbon feedstream" as used herein are equivalent and are defined as any stream containing at least 75 wt % hydrocarbons. These hydrocarbon feedstreams may be comprised of either "petroleum-based hydrocarbons", "biofuel hydrocarbons", or combinations thereof. The "petroleum-based hydrocarbons" are hydrocarbons obtained or derived hydrocarbonaceous materials from geological formations such as, but not limited to, crude oils, and oils derived from coal, tar sands, or bitumens, as well as any intermediate hydrocarbon or final hydrocarbon product derived from these sources. These are generally considered as non-renewable hydrocarbon sources.

As used herein, the terms "heavy hydrocarbon" or "heavy hydrocarbon stream" are equivalent and are defined herein as a subset of "petroleum-based hydrocarbons" and include hydrocarbon-containing streams containing at least 75 wt % hydrocarbons and having an API gravity of less than 20. Exemplary heavy hydrocarbon streams for use in the present invention include, but are not limited to low API gravity, high sulfur, high viscosity crudes; tar sands bitumen; liquid hydrocarbons derived from tar sands bitumen, coal, or oil shale; as well as petrochemical refinery heavy intermediate fractions, such as atmospheric resids, vacuum resids, and other similar intermediate feedstreams and mixtures thereof containing boiling point materials above about 343° C. (650° F.). Heavy hydrocarbon streams may also include a blend of the hydrocarbons listed above with lighter hydrocarbon streams for control of certain properties for transport or sale, such as, but not limited to fuel oils and crude blends.

As used herein, the term "biofuel hydrocarbons" or "biofuels" are equivalent and are a subset of hydrocarbon streams, and are defined as hydrocarbon-containing streams wherein at least 50 wt % of the hydrocarbon material in the hydrocarbon-containing stream is derived from renewable biomass resources. These biomass resources include any plant or animal derived organic matter, such as dedicated energy crops and trees, agricultural food and feed crops, agricultural crop wastes and residues, wood wastes and residues, aquatic plants, algae, fungi, plant oils, animal oils, animal tissues, animal wastes, municipal wastes, and other waste materials. Biofuels may include, but are not limited to, hydrocarbons in the middle distillate range, diesels, kerosenes, gasoline, gasoline fractions, biodiesel, biojet fuel, biogasolines and combinations thereof.

As used herein, the term "plant oil" is a subset of biofuels and is defined as a hydrocarbon-containing material derived from plant sources, such as agricultural crops and forest products, as well as wastes, effluents and residues from the processing of such materials. Plant oils may include vegetable oils. Examples of plant oils may include, but are not limited to, canola oil, sunflower oil, soybean oil, rapeseed oil, mustard seed oil, palm oil, corn oil, soya oil, linseed oil, peanut oil, coconut oil, corn oil, olive oil, and combinations thereof.

As used herein, the term "animal oil" is a subset of biofuels and is defined as a hydrocarbon-containing material derived animal sources, as well as wastes, effluents and residues from the processing of such materials. Examples of animal oils may include, but are not limited to, animal fats, yellow grease, animal tallow, pork fats, pork oils, chicken fats, chicken oils, mutton fats, mutton oils, beef fats, beef oils, and combinations thereof.

As used herein, the terms "interstitial metal hydride" or "iMeH" are equivalents and are defined as materials that are composed of alloyed metals combined with atomic hydrogen, wherein the atomic hydrogen occupies interstices within the metal alloy matrix. The terms "interstitial metal hydride" or "iMeH" are intended to refer solely to the iMeH component or components of the catalysts of the invention.

The term "Group VI/Group VIII metal sulfide," as used herein, refers to a compound comprising at least one Group VI metal, at least one Group VIII metal, and sulfur. Groups VI and VIII refer to the older IUPAC groupings of the Periodic Table. Group VI includes the elements chromium, molybdenum and tungsten. Group VIII includes the elements iron, cobalt, nickel, ruthenium, rhodium, palladium, osmium, iridium and platinum. Exemplary Group VI/Group VIII metal sulfides include, but are not limited to, $CoMoS_x$ and $NiMoS_x$. The subscript "x" as used herein indicates that the material, in particular the sulfur in the material, may or may not be stoichiometrically exact.

The terms "high pressure/high severity" and "severe" hydroprocessing conditions and/or processes are equivalents as used herein and are defined as hydroprocessing processes wherein a hydrocarbon feedstream is contacted with a hydroprocessing catalyst in the presence of hydrogen at process conditions of at least 400 psig and at least 200° C.

The term "activity" as used herein, when referring to a catalyst of the invention, refers to the amount of a reactant consumed or the amount of a product produced per unit amount of time under a given set of reaction conditions. The activity may be measured, for example, by determining a rate constant. In a non-limiting example, the activity of a catalyst described herein may be measured by determining the first order rate constant for the disappearance of a compound in a model feed, e.g., the conversion (or disappearance) of dibenzothiophene, 4,6-diethyldibenzothiophene or 1n-dodecylnaphthalene.

The term "hydroprocessing" (or equivalent term "hydrotreating") as used herein is a general term and is defined as any catalytic process involving hydrogen. This includes the reaction of any petroleum fraction with hydrogen in the presence of a catalyst. This includes processes which remove undesirable impurities such as sulfur, nitrogen, metals, and unsaturated compounds in the presence of hydrogen and a catalyst. Examples include, but are not limited to, hydrogenation, hydrocracking, hydrodesulfurization, hydrodenitrogenation hydrodemetalization, and catalytic hydrodewaxing.

The terms "upgrade", "upgrading" and "upgraded", when used in conjunction with a hydrocarbon feedstream, describes a hydrocarbon feedstream that is or has been subjected to hydroprocessing, or a resulting material or product stream, having a reduction in the molecular weight of the hydrocarbon compounds in the hydrocarbon feedstream, an increase in hydrogen content of the hydrocarbon compounds in the hydrocarbon feedstream, a reduction in the boiling point range of the hydrocarbon feedstream, and/or a reduction in the quantity of impurities such as sulfur, nitrogen, and metals.

The term "hydrogenation" as used herein is defined as any process wherein a hydrocarbon feedstream is contacted with a catalyst and hydrogen at an elevated pressure and temperature wherein hydrogen is chemically added to at least a portion of the hydrocarbon compounds in the hydrocarbon feedstream, thereby increasing the hydrogen content of the hydrocarbon compounds. Exemplary hydrogenation applications include the hydrogen addition to "unsaturated" olefinic or aromatic hydrocarbon compounds (e.g., olefin hydrogenation or aromatic hydrogenation). Hydrogenation is a subset of hydroprocessing processes.

The term "hydrocracking" as used herein is defined as any process wherein a hydrocarbon feedstream is contacted with a catalyst and hydrogen at an elevated pressure and temperature wherein at least a portion of the hydrocarbon feedstream is converted into lower-boiling point products, thereby resulting in an overall lower average boiling point product stream based on wt %. Hydrocracking is a subset of hydroprocessing processes.

The term "hydrodesulfurization" or "HDS" as used herein is defined as a process in which a hydrocarbon feedstream is contacted with a catalyst and hydrogen at an elevated pressure and temperature wherein at least a portion the sulfur elements or compounds present in hydrocarbon feedstream are removed, thereby resulting in at least one hydrocarbon product with a lower sulfur content than the hydrocarbon feedstream. Hydrodesulfurization is a subset of hydroprocessing processes.

The term "hydrodenitrogenation" or "HDN" as used herein is defined as a process in which a hydrocarbon feedstream is contacted with a catalyst and hydrogen at an elevated pressure and temperature wherein at least a portion the nitrogen elements or compounds present in hydrocarbon feedstream are removed, thereby resulting in at least one hydrocarbon product with a lower nitrogen content than the hydrocarbon feedstream. Hydrodenitrogenation is a subset of hydroprocessing processes.

The term "hydrodemetalization" or "HDM" as used herein is defined as a process in which a hydrocarbon feedstream is contacted with a catalyst and hydrogen at an elevated pressure and temperature wherein at least a portion the metal elements or compounds present in hydrocarbon feedstream are removed, thereby resulting in at least one hydrocarbon product with a lower metal content than the hydrocarbon feedstream. Hydrodemetalization is a subset of hydroprocessing processes.

The term "catalytic hydrodewaxing" as used herein is defined as a catalytic hydrocracking process which uses molecular sieves, suitably zeolites, to selectively hydrocrack and/or isomerize waxes (i.e., long chain paraffinic molecules with greater than about 22 carbon molecules) present in the hydrocarbon streams to smaller carbon content molecules, thereby resulting in an overall lower average boiling point product stream based on wt %. Catalytic hydrodewaxing is a subset of hydroprocessing processes.

It is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

Also, it is to be understood that the phraseology and terminology used herein is for the purpose of description and should not be regarded as limiting. The use of "comprising," "including," "having," and variations thereof herein is meant to encompass the items listed thereafter and equivalents thereof as well as additional items. "Comprising" encompasses the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method.

Interstitial Metal Hydrides

The catalysts of the present invention include interstitial metal hydrides (iMeHs), which are materials that are composed of alloyed metals combined with atomic hydrogen, wherein the atomic hydrogen is stored interstitially within the metal alloy matrix.

U.S. Pat. Nos. 7,157,401 and 7,387,712 to Purta et al., which are incorporated herein by reference in their entireties, disclose hydroprocessing processes using iMeH catalysts. In these processes, hydrocarbon streams are contacted with iMeH catalysts under mild conditions (e.g., 200° C. at 50 psig), optionally in the presence of microwaves, for the hydrogenation of hydrocarbon molecules. In particular, these patents disclose three specific compositions of iMeHs: Cat 100 (or "$AT_5$ type"), CAT 200 (or "$A_2T_{14}B$ type") and CAT 300 (or "$A_2T$ type").

U.S. Patent Application No. 61/281,965, which is incorporated herein by reference in its entirety, discloses "high severity hydroprocessing iMeHs," which provide improved hydroprocessing of hydrocarbon streams at high temperatures (above 200° C.) and high pressures (above 400 psig) associated with many commercial hydroprocessing processes. The high severity hydroprocessing iMeHs have both significant hydrogen storage capacities under the processing conditions (i.e., the iMeHs are not depleted of hydrogen), as well as high hydrogen kinetics rates for the transfer of hydrogen into and out of the iMeHs under the hydroprocessing conditions (i.e., hydrogen atoms move in and out of the iMeH at a rapid rate). In particular, this application discloses specific compositions of iMeHs: Cat 400 (or "$AT_{2\pm d1\pm d2}$ type").

The metal alloy matrix of the iMeH can have a crystalline or amorphous structure. The iMeH is especially suited to accommodating monatomic hydrogen extracted from molecular hydrogen. The hydrogen atoms occupy interstitial sites in the alloy lattice of the iMeH. The quantity of atomic hydrogen in the interstitial metallic hydrides has a measurable value, which is a function of alloy composition, and operating temperature and hydrogen partial pressure. In an iMeH, the ratio of hydrogen to metal atoms may vary over a range and may not be expressible as a ratio of small whole numbers. The iMeH components of the catalysts of the present invention are able to dissociate diatomic hydrogen molecules at the surface into monatomic hydrogen (i.e. hydrogen atoms), absorb copious amounts of monatomic hydrogen thus produced into the metal alloy, and desorb the monatomic hydrogen under the appropriate conditions. A heat of absorption is produced when the molecular hydrogen dissociates into atomic hydrogen and the hydrogen atoms position themselves interstitially in the structure of the material. Additional energy at a suitable steady state process temperature and pressure is required for the release of monatomic hydrogen from within the iMeH. This energy can be derived from the process heat of reaction or from external application of energy or both.

The iMeHs are produced by preparing samples of the constituent metals in the desired proportions, and combining them and heating them so that they melt together homogeneously to produce a metal alloy. The resulting metal alloy may then be exposed to hydrogen at a temperature and pressure characteristic of the alloy so that the metal alloy takes up the hydrogen in monatomic form.

The iMeH component materials of the present invention are typically prepared by a volumetric (gas to solid alloy) method at a known temperature and pressure using a stainless steel reactor. The metallic hydride will absorb hydrogen with an exothermic reaction. This hydrogenation process is reversible according to the following chemical reaction schematic:

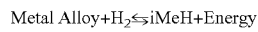

Metal Alloy+$H_2$⇌iMeH+Energy

As noted, the hydrogen uptake/release is accompanied by an exothermic/endothermic exchange of energy. Hydrogen uptake/release is also accompanied by volume expansion/contraction of the iMeH which under certain conditions can be high as about 20 to 25 vol %. During this process, hydrogen atoms will occupy interstitial sites in the alloy lattice. This hydrogen absorption/desorption by an iMeH can be measured and characterized in a Pressure-Composition-Temperature ("PCT") plot or graph.

The metal alloy from which an iMeH is produced can be prepared by mechanical or induction-heated alloying processes. The metal alloy can be stoichiometric or non-stoichiometric. Non-stoichiometric compounds are compounds that exhibit wide compositional variations from ideal stoichiometry. Non-stoichiometric systems contain excess elements, which can significantly influence the phase stability of the metallic hydrides. The iMeH is produced from a metal alloy by subjecting the alloy to hydrogen at a pressure and temperature that is a characteristic of the particular alloy.

The iMeH catalysts of the present invention can be selected to have a desired lattice structure and thermodynamic properties, such as the applied pressure and temperature at which they can be charged and the operating pressure and temperature at which they can be discharged. These working thermodynamic parameters can be modified and fine tuned by an appropriate alloying method, and therefore, the composition of the catalysts can be designed for use in a particular catalytic process.

It should be noted that the coated iMeH catalysts of the present invention can be prepared by starting with any interstitial metal hydride, and such compositions of the present invention are not limited to the specific iMeHs disclosed herein. It is believed herein that the novel coating process and the benefits achieved by the invention herein will operate with any known interstitial metal hydride. Exemplary embodiments of the iMeH suitably include a "CAT 100," "CAT 200," or "CAT 300" catalyst. The compositional formulations of CAT 100, CAT 200 and CAT 300 are shown as follows.

CAT 100
  $AT_5$ Type
  Crystal Structure: Hexagonal
  General Formula: $A_{1-x}M_xT_{5-y-z}B_yC_z$
  wherein:
  A=Mm (mischmetal); T=Ni; M=La, Pr, Nd or Ce; B=Co; C=Mn, Al or Cr; and
  x=0.0 to 1.0; y=0.0 to 2.5; and z=0.0 to 0.5.

CAT 200
  $A_2T_{14}B$ Type
  Crystal Structure: Tetragonal
  General Formula: $A_{2-x}M_xT_{14-y}C_yD_zB$
  wherein:
  A=Nd or Pr; T=Fe; M=La, Pr, Nd or Ce; B=Boron; C=Co; D=Cr, Ni or Mn; and
  x=0.0 to 2.0; y=0.0 to 14; and z=0.0 to 3.0.

CAT 300
  $A_2T$ Type
  Crystal Structure: Monoclinic
  General Formula: $A_{2-x}M_xT_{1-y}B_y$
  wherein:
  A=Mg; T=Ni or Cu; M=La; B=Fe or Co;
  x=0.0 to 0.5; and y=0.0 to 0.5.

In certain embodiments, the iMeH is a "CAT 400" catalyst composition. The composition of the CAT 400 elements can be either stoichiometric or non-stoichiometric. The compositional formulations of CAT 400 are shown as follows. It should be noted that when $d_1$=0 and $d_2$=0, a stoichiometric composition of CAT 400 is shown.

CAT 400 (Stoichiometric & Non-Stoichiometric Compositions)
  $AT_{2\pm d1 \pm d2}$ Type
  Crystal Structure: Compositionally dependent; Cubic Laves phase-C15 (MgCu$_2$-type) and Hexagonal Laves phase-C14 (MgZn$_2$-type)
  General Formula: $A_{1-x}B_xT_{(2-y)\pm d1}C_{y\pm d2}$
  wherein:
  A=Nd or Zr; B=at least one of La, Ce, Pr, Gd, Tb, Dy, Er, Ho, Ti and Hf; T=at least one of Fe and V; C=at least one of Cr, Mn, Fe, Co, Ni and Cu; and
  x=0.0 to 1.0; and y=0.0 to 2.0; and
  $d_1$=0.00 to 0.2; and $d_2$=0.00 to 0.2

In an exemplary embodiment of CAT 400, $d_1$=0; and $d_2$=0 (stoichiometric only compositions).

In an exemplary embodiment of CAT 400, $d_1$=0.05 to 0.2; and $d_2$=0.05 to 0.2 (non-stoichiometric only compositions).

In an exemplary embodiment of CAT 400, A=Zr and T=V.

In another exemplary embodiment of CAT 400, A=Zr and T=V; x=0.2 to 0.6; and y=0.2 to 0.6.

In another exemplary embodiment of CAT 400, A=Zr; B=at least one of Ti and Hf; T=V; C=at least one of Mn and Fe.

In a further exemplary embodiment of CAT 400, A=Nd or Zr; B=at least one of La, Ce, Pr, Gd, Tb, Dy, Er, Ho, Ti and Hf; T=at least one of Fe and V; C=at least one of Cr, Mn, Fe, Co, Ni and Cu; x=0.2 to 0.6; and y=0.2 to 0.6.

In a highly suitable embodiment of CAT 400, A=Zr; B=at least one of Ti and Hf; T=V; C=at least one of Mn and Fe; x=0.2 to 0.6; and y=0.2 to 0.6.

In another highly suitable embodiment of CAT 400, A=Zr; B=at least one of Ti and Hf; T=V; C=at least one of Mn and Fe; x=0.2 to 0.6; and y=0.

In another highly suitable embodiment, of CAT 400, y=0.

The CAT 400 iMeHs have high hydrogen storage capacities and high hydrogen kinetics rates at the high temperatures and pressures at which most commercial hydroprocessing processes operate. In particular, these high severity processes include, but are not limited to, hydrogenation, hydrocracking, hydrodesulfurization, hydrodenitrogenation, and hydrodemetalization processes.

Group VI/Group VIII Metal Sulfides

The catalysts of the present invention include an iMeH with a Group VI/Group VIII metal sulfide coated on its surface. The Group VI/Group VIII metal sulfide includes at least one Group VI metal, at least one Group VIII metal, and sulfur. In some embodiments, the Group VI metal is selected from Mo and W. In some embodiments, the Group VIII metal is selected from Fe, Co, Ni, Pd, and Pt. In exemplary embodiments, the Group VI metal is Mo and the Group VIII metal is selected from Co and Ni. Non-limiting examples of Group VI/Group VIII metal sulfides that may be used in the catalysts of the invention are $CoMoS_x$ and $NiMoS_x$.

While not being bound by any particular theory, it is believed that the iMeH components of the catalysts can absorb and release hydrogen in its monatomic state which is more reactive with the hydrocarbons in the process than the diatomic hydrogen that is typically present. However, in light of the present invention, it is believed that when the monatomic hydrogen is released from the iMeH surface, it may also be highly reactive with other monatomic hydrogen in the system. Therefore, in the present invention, having additional catalytic elements coated directly on the surface of the iMeH may shorten the spillover pathway between the iMeH and the metal sulfide resulting in the unexpected catalytic activities shown in the examples herein. The monatomic hydrogen may then react with the hydrocarbon molecules or heteroatom-containing molecules (such as sulfur, nitrogen, or metals) in the feedstream, improving the efficiency of monatomic hydrogen utilization. The resulting products (e.g., hydrogen sulfide) can then be easily removed from the hydroprocessed product stream. The increase in active monatomic hydrogen may also allow for attack on surface coke accumulation, improving the long-term stability of the catalyst.

In some embodiments of the catalyst of the present invention, the Group VI/Group VIII metal sulfide is coated on the surface of the interstitial metal hydride by in-situ decomposition (e.g., thermal decomposition) of at least one Group VI metal salt and at least one Group VIII metal salt. In some embodiments, the Group VI metal salt is selected from Mo and W salts. In some embodiments, the Group VIII metal salt is selected from Fe, Co, Ni, Pd, and Pt salts. In a more suitable embodiment, the Group VI metal salt is a Mo salt and the Group VIII metal salt is selected from Co and Ni salts. At least one of the metal salts comprises sulfur. The sulfur may be present in any form, such as, for example, a thiolate or a sulfide anion. For example, Group VI metal salt may be a polythiomolybdate salt such as ammonium polythiomolybdate.

In some embodiments of the catalyst of the present invention, the iMeH and the Group VI/Group VIII metal sulfide are suitably present in the catalyst in a ratio of about 20:80 by weight to about 80:20 by weight. More suitably, the iMeH and the Group VI/Group VIII metal sulfide are present in the catalyst in a ratio of about 35:65 by weight to about 65:35 by weight. For example, the iMeH and the Group VI/Group VIII metal sulfide may be present in the catalyst in a ratio of about 20:80, 35:65, 50:50, 65:35 or 80:20 by weight. In a most exemplary embodiment of the present invention, the iMeH and the Group VI/Group VIII metal sulfide are present in the catalyst in a ratio of about 50:50 by weight. While not bound by theory, the catalytic activity may be optimized when the rate of monatomic hydrogen produced by the iMeH matches the rate of hydrogen consumption on the Group VI/Group VIII metal sulfide.

After depositing the Group VI/Group VIII metal sulfide on the surface of the iMeH, the monatomic hydrogen uptake by the catalyst of the invention can be determined. For example, X-ray Powder Diffraction (XRD) data for certain catalysts of the invention are shown in FIG. 1. The peaks in the spectrum confirm that monatomic hydrogen is still able to be absorbed by the iMeH after coating with the metal sulfide. As such, it is believed that the applied coating of the present invention unexpectedly provides a porous medium through which the hydrogen (or monatomic hydrogen) can move in and out of the iMeH component.

Catalyst Activities

The activities of catalysts of the invention may be assayed using model feeds, for example, a poly-alpha-olefin ("PAO") based model feed. The model feed may be spiked with certain molecules in order to assay certain activities, such as hydrogenation activity and hydrodesulfurization (HDS) activity. Non-limiting examples of such model compounds include HDS substrates dibenzothiophene (DBT) and 4,6-diethyldibenzothiophene (DEDBT), and hydrogenation substrates 1n-dodecylnaphthalene ($C_{12}$ naphthalene). The activities of the catalysts may be determined by measuring the first order rate constants for the conversion (or disappearance) of these compounds from the model feeds.

In exemplary catalysts of the present invention, the activities of the catalysts may be greater than the sum of the activity of the iMeH alone and the activity of the Group VI/Group VIII metal sulfide alone. Even more surprising is that the catalysts of the present invention provide improved and synergistic effects over catalysts made of similar compositions, but which have been pressed together versus the unique coating used for the catalysts of the present invention described herein. This synergistic effect when the Group VI/Group VIII metal sulfide is coated directly on the surface of the iMeH may be observed by comparing the activity of the catalyst of the invention with an iMeH alone, a metal sulfide alone, and a preparation in which particles of an iMeH are combined with particles of a Group VI/Group VIII metal sulfide, for example, by pressing the components together in a binder.

While not being bound by any particular theory, the extensive direct contact between the iMeH and the Group VI/Group VIII metal sulfide, generated by coating the Group VI/Group VIII metal sulfide directly on the surface of the iMeH, may shorten the spillover pathway between the iMeH and the metal sulfide. This may improve the efficiency of monatomic hydrogen utilization in the catalytic reaction.

Catalyst Formulations

The Group VI/Group VIII metal sulfide iMeH catalysts as described herein may be used alone or they can be combined with other components such as additional catalyst materials or supports. For example, the catalysts can be combined with known hydroprocessing catalysts such as noble metals, metal oxides, metal sulfides, zeolitic acid or base sites to further promote hydroprocessing of feedstocks such as organic compounds. The catalysts of the invention can be combined with other hydroprocessing materials in a variety of ways to build an optimized catalyst for a particular reaction or function. Key to the processing steps is to minimize the exposure of the catalyst to oxygen and/or water vapor at elevated temperatures (e.g., above 25° C.) for extended periods of time. Exposure can be minimized by use of desiccants and by blanketing atmospheres of inert gases such as nitrogen and argon.

It is important that the catalyst be limited in its exposure to either air and/or water as the iMeH in particular is prone to forming a strong oxide layer when exposed to oxygen sources. This oxygen layer can create a significant barrier on the iMeH surface which limits the transfer of monatomic hydrogen between the feed environment and the iMeH crystal lattice. Exposure to oxygen and water can be minimized by surrounding the catalyst with a blanketing atmosphere such as nitrogen or argon that is pure or has been treated by a dryer or desiccant to remove water content. These inert atmospheres should be used in the fabrication, transportation, and reactor loading sequences of the operation to minimize oxidation of the catalysts.

The catalysts can be combined with a support and optionally other catalytic elements to produce a composite catalyst. The support provides for the physical dispersion of the catalysts, providing greater surface area and ease of handling. The support also serves to increase the surface area of the active catalytic elements, and thereby, increase the process reaction rates. The support can also add acidic or basic sites that can enhance the catalytic activity of other catalyst components or acts as catalysts themselves. The support also serves to disperse the catalytic sites so as to prevent arcing in the presence of a strong electric or magnetic fields that may be used to expedite catalytic action.

The support may be an inorganic oxide, nitride, carbide, a metal, a carbon, or combinations of these materials. In certain embodiments of the present invention, the support includes alumina, silica, titania, zirconia, MCM-41 or combinations thereof. The catalysts and optional additional catalytic elements can be dispersed as mechanically mixed powders, or can be chemically dispersed, impregnated or deposited. When mixed powders are used in the present invention, the powder particle size is controlled to provide a powder that has particles that are small enough to provide suitable surface area and reactivity, but not so fine as to produce significant surface oxidation.

Other catalytic elements included in the catalyst systems of the present invention may be noble metals such as platinum or palladium, Group VI and VIII metal oxides and/or metal sulfides, and zeolite acid or base sites. A hydroprocessing component and a hydrocracking component used in combination with the catalyst may be one or more of these catalytic elements. Both the combination of a catalyst powder with a support, which may or may not provide an additional catalyst function (i.e. at catalytically active or inert support), or a catalyst dispersed onto a hydroprocessing catalytic powder, can be especially effective for hydrocracking in a fluidized bed or ebullating bed reactor.

The catalyst may further include a radio frequency or microwave absorber, which may be in thermal contact with the interstitial metal hydride. The separate radio frequency or microwave absorber absorbs the energy and transfers it to the iMeH through thermal conduction or convection. These absorbers may be added metal elements or metal compounds with high dielectric constants, and may be, for example, one or more compounds such as silicon carbide, iron silicide, nickel oxide, and tungsten carbide. In another embodiment of the invention, the iMeH component functions as the primary radio frequency or microwave energy absorber. When used with microwave enhancement, the iMeH component is sufficiently dispersed within the catalyst and feedstock combination to avoid hot spots and arcing generally associated with the introduction of metals into a microwave or RF field.

Hydroprocessing

The catalysts of the invention may be used in a hydroprocessing process. Unless further described in detail herein, the term "hydroprocessing" may apply to any process wherein hydrogen, preferably molecular hydrogen ($H_2$), is contacted with a hydrocarbon-containing feedstream and a catalyst as described herein, under sufficient conditions for the hydrogen to react with the hydrocarbon-containing feedstream to form new hydrocarbon compounds. Such hydroprocessing processes are referred to in the art such terms as, but not limited to, hydrodesulfurization, hydrodenitrogenation, hydrodemetalization, hydrocracking, hydroisomerization, hydrogenation, and hydrodewaxing processes.

In an exemplary embodiment of the present invention, a hydrocarbon stream and/or a heavy hydrocarbon stream containing at least 1 wt % sulfur and more suitably at least 3 wt % sulfur is contacted with a catalyst of the invention in the presence of hydrogen at a process conditions of at least 200° C. and at least 400 psig. In other exemplary embodiments of the present invention, the hydrocarbon stream and/or the heavy hydrocarbon stream that is desulfurized in the present process contains polycyclic sulfur heteroatom complexes which are difficult to desulfurize by conventional methods.

Although not required for the use of the present invention, the catalytic activity of the catalysts of the present invention can be enhanced and controlled by exposing the catalysts to radio frequency ("RF") energy (about $3 \times 10^5$ Hz to about $3 \times 10^8$ Hz) or microwave energy (about $3 \times 10^8$ Hz to about $3 \times 10^{12}$ Hz), either in the absence of, the presence of, or in sequence with conventional fuel fired heating or resistive heating. The RF or microwave energy can provide for a significant increase in hydroprocessing efficiency in comparison to conventional heating. Furthermore, the microwave energy can be modulated and controlled in such a manner as to optimize the reaction exchange of the monatomic hydrogen from the iMeH. When used with microwave enhancement, the iMeH component is sufficiently dispersed within the catalyst and feedstock combination to avoid hot spots and arcing generally associated with the introduction of metals into a microwave or RF field.

The selective use of RF or microwave energy aids in the release of the iMeH monatomic hydrogen. It is cost effective to maximize the use of fossil fuels to pre-heat the feedstocks to near reaction temperatures, and use minimum RF or microwave energy to drive and control the hydroprocessing reactions. Ideally, there will be a minimized or zero net temperature increase from the RF or microwave energy into the catalyst support, if present, or into the feedstock because this energy is primarily targeted into the iMeH to enhance the reaction exchange of monatomic hydrogen. Selective coupling of the RF or microwave energy is accomplished through selection and control of the relative dielectric parameters of the catalyst's components and the feedstock. This results in efficient, economically viable catalytic processes, which are enhanced using microwaves.

Figure 4:
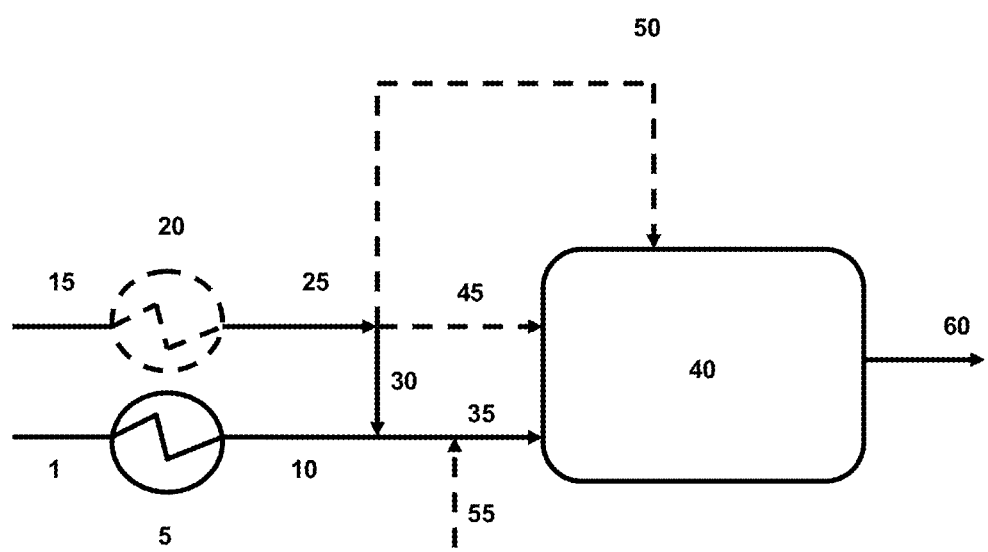
FIG. 4 is a simplified schematic of an exemplary reaction process configuration using the catalysts of the present invention.

A schematic of an exemplary process configuration using the catalysts of the present invention is shown in FIG. 4 wherein the incoming hydrocarbon feedstream is heated to a target temperature prior to entering the reactor and the RF or microwave energy is introduced into the reactor itself. FIG. 4 shows an exemplary embodiment of the present invention wherein a single stage reactor unit is used. Here, a hydrocarbon stream (1) is heated to a predetermined elevated temperature using a fired heater or heat exchange unit (5) to produce a heated hydrocarbon feedstream (10). Similarly a hydrogen-rich stream (15) can be heated, if necessary, a fired heater or heat exchange unit (20) to produce a heated hydrogen-rich stream (25). The term "hydrogen-rich stream" as used herein is a stream containing at least 50 mole percent (mol %) of hydrogen. In an exemplary embodiment, at least a portion of the heated hydrogen-rich stream (25) is combined via (30) with the heated hydrocarbon feedstream (10) to form a heated combined hydrocarbon feedstream (35) which is fed to the hydroprocessing reactor unit (40). In an optional embodiment, some, or all, of the heated hydrogen-rich stream enters directly into the hydroprocessing reactor unit (40) via line (45). Even more suitably, at least some of the heated hydrogen-rich stream (25) is fed to various points (50) within the hydroprocessing reactor unit (40) itself. This added hydrogen in the reaction process assists in maintaining a sufficient hydrogen concentration within the reactor itself as well as providing fresh hydrogen for absorption/desorption by catalysts.

Continuing with FIG. 4, in an exemplary embodiment, the catalyst is substantially maintained in the hydroprocessing reactor unit (40) itself. However, in other embodiments, a portion or all of the catalyst is introduced into the feedstream entering the reactor (55) as a slurry or particulate catalyst. Although the catalyst is shown entering the feedstream system at point (55), the catalyst can be entered in to the hydrocarbon feedstream, the heated hydrocarbon feedstream, and/or the hydrogen-rich stream at any point prior to entering the hydroprocessing reactor unit (40). In an exemplary embodiment, RF or microwave energy is supplied to the catalyst/hydrocarbon/hydrogen mixture in the hydroprocessing reactor (40) to assist in promoting the absorption and desorption of the monatomic hydrogen in the catalysts. Continuous, pulsed, frequency modulated and/or two or more frequencies of RF or microwave energy may be used.

A reaction product stream (60) is withdrawn from the hydroprocessing reactor (40). This stream will typically contain some gaseous hydrocarbon products and hydrogen along with an upgraded liquid hydrocarbon product stream. These gaseous products can be separated by processes known in the art and a liquid hydrocarbon product stream with improved product qualities is retrieved.

In some embodiments, the operating (or "reaction") conditions are at least 400 psig and at least 200° C. More suitable reaction conditions are at least 600 psig and at least 250° C. Suitable hydrogen partial pressures are at least about 350 psia, and even more suitably at least about 500 psia. Most suitably, the reaction conditions are within the operating envelope of about 200° C. to about 450° C. with an operating pressure of from about 400 psig to about 2500 psig.

Hydroprocessing configurations using the catalysts of the present invention, which incorporate additional process stages and hydroprocessing reactors to those described above may be also be used in the processes of the present invention and may also be coupled with interstage and/or inter-reactor separations steps to separate liquid hydrocarbon-containing reaction streams from gaseous hydrocarbon-containing reaction streams and/or to incorporate separation steps for separating the catalysts from the hydrocarbons in order to improve overall selectivity and conversion of the final hydrocarbon products as would be within the purview of one of skill in the art in light of the present invention disclosure.

The catalysts of the present invention can be used in any hydroprocessing process. Specific hydroprocessing processes in which the catalysts of the present invention can be used include, but are not limited to the following processes: hydrogenation, hydrocracking, hydrodesulfurization, hydrodenitrogenation, hydrodemetalization and catalytic hydrodewaxing.

Although the present invention has been described in terms of specific embodiments, it is not so limited. Suitable alterations and modifications for operation under specific conditions will be apparent to those skilled in the art. It is therefore intended that the following claims be interpreted as covering all such alterations and modifications as fall within the true spirit and scope of the invention.

EXAMPLES

Example 1

This example describes how the CAT 400 iMeH components used in the Examples herein, including those used in the catalysts of the invention, were fabricated. While the coated iMeH compositions of present invention are believed to operate with any interstitial metal hydride (iMeH), the CAT 400 composition samples were used throughout in the testing of these Examples to provide proof of concept on a comparative standard basis.

Chemical Compositions

The chemical composition of the CAT 400 iMeHs prepared in the Examples was $ZrV_2$.

iMeH Sample Preparations

The metal alloys were prepared by melting together the appropriate amounts of metals with purities of 99.9% (from Alfa Aesar/Johnson Matthey Company™) in an argon atmosphere using water cooled copper hearth argon arc furnace Model CENTORR® from Centorr Vacuum Industries™, Nashua, N.H. Each arc-melted ingot was flipped over and re-melted three times and was normally held in the liquid state for approximately 30 seconds to insure complete mixing of the starting materials.

To obtain single phase materials, the cast samples were sealed in quartz tubes, filled with 1/3 atmosphere of argon gas and annealed at 950° C. for a period of 3 to 5 days using a Thermo scientific LindbergBlue™ tube furnace. The samples in the tubes were water quenched to avoid a possible phase transition during the cooling process.

The crystal structures of the samples were determined by powder X-ray diffraction.

CAT 400 is based on $ZrV_2$ with a purity of about 99.9%. The reduction in the sample weight was negligible. The crystal structure was determined to be single phase with cubic Laves phase C15 ($MgCu_2$) type for $ZrV_2$ alloys.

The metal alloy bulk was crushed manually to an average particle size of approximately 200 μm (microns). The hard alloy samples were milled mechanically at cryogenic temperatures (approximately 80° K) and then were attrited. All samples were sieved to under approximately 200 μm (microns).

All particle size preparations of the samples were performed under inert nitrogen atmosphere conditions. The average particle size distribution was obtained using Horiba Laser-La-920® Particle Analyzer, from HORIBA Instruments™, Inc., Irvine, Calif.

iMeH Catalyst Activation

Approximately 4 to 5 grams of metal alloy powder with known molecular weight was then placed into the stainless steel reactor connected to the Hy-Energy™ system. The reactor was then purged with hydrogen three times. $H_2$ pressure is introduced to the sample chamber from about 500 psig to about 800 psig at ambient temperature (i.e., 25° C.) and a waiting period is given to observe if any absorption takes place. A pressure drop in the reactor, generally in the range of about 20 psig depending on the amount of hydrogen absorbed, will indicate the hydrogen activation process. Typical waiting period times are from 10 to 30 minutes. If no absorption occurs, then the temperature is raised to about 250° C. The temperature needed to activate the sample depends on the active surface of the alloy. The sample starts absorbing hydrogen which is an exothermic process. The hydrogen activated sample is then cooled down to ambient temperature and pressure to achieve maximum hydrogen absorption.

Example 2

This example describes how the Group VI/Group VIII metal sulfides were deposited on the surfaces of the CAT 400 iMeH components of Example 1 to form exemplary catalysts of the invention. In this example, the CAT 400 formulation was $ZrV_2$ as described in Example 1; the Group VI/Group VIII metal sulfide is $CoMoS_x$.

Preparation of the $CoMoS_x/ZrV_2$ Catalyst (Labeled Herein as the "CoMoSx (Coated)/Hydride Catalyst")

$CoMoS_x/ZrV_2$ samples were prepared by mixing, grinding Co and Mo thio salts with $ZrV_2$. The mixture was then calcined in nitrogen. Inside a nitrogen atmospheric glove box, appropriate amount of $ZrV_2$ metal hydrides were mixed with appropriate amounts of $(NH_4)_2Mo_3S_{13}$ (ammonium polythiomolybdate) and $Co[(C_2H_5)_2NCS_2]_2$ (cobalt diethyldithiocarbamate). The sample was placed in a nitrogen containing bag and pressed under 30 tons for 10 min. The pressed sample disks were broken into pieces. The chunks of the sample pieces are placed inside a tube furnace. The furnace was purged in $N_2$ for 2 hrs. The tube furnace was ramped from room temperature to 392° F. at rate of 10° F./min and held at 392° F. for 2 hrs. After holding, the furnace was ramped again from 392 to 650° F. at 10° F./min and held at 650° F. for 3 hrs. The reactor system was cooled off in nitrogen flow to room temperature. Catalyst samples with compositions of 0, 20%, 35%, 50%, 65%, 80% and 100% by weight of $CoMoS_x$ on $ZrV_2$ iMeH were prepared.

Table 1 lists the calculated and ICP analyzed elemental results of the samples of 18.4% $CoMoS_x$+81.6% $ZrV_2$ and 49.2% $CoMoS_x$+50.8% $ZrV_2$ (examples of "CoMoSx (coated)/hydride catalysts"). In these two samples, sulfur contents are ~23-30% over stoichiometry if sulfur is only counted as in the compounds of $Co_9S_8$ and $MoS_2$. Sulfur resulted from decomposition of CoMo thio salts may spillover onto Zr and V metal hydrides and resulting in partial sulfidation of zirconium and vanadium. Sulfur surplus in the samples of $CoMoS_x/ZrV_2$ may be associated with the formation of Zr and V sulfides.

TABLE 1

Elemental Compositions of $CoMoS_x/ZrV_2$ Samples

|  | Co | Mo | S | Zr | V |
|---|---|---|---|---|---|
| 18.4% $CoMoS_x$ + 81.6% $ZrV_2$ | | | | | |
| Calculated component contents | 2.6% | 8.6% | 7.1% | 38.6% | 43.1% |
| Analyzed component contents | 1.8% | 7.2% | 8.8% | 39.8% | 31.2% |
| 49.2% $CoMoS_x$ + 50.8% $ZrV_2$ | | | | | |
| Calculated component contents | 7.1% | 23.2% | 18.9% | 24.0% | 26.8% |
| Analyzed component contents | 5.2% | 20.4% | 24.5% | 20.9% | 23.0% |

X-Ray Powder Diffraction

XRD analyses of the samples above were obtained using a Bruker D4 Endeavor, manufactured by Bruker AXS and equipped with a Vantec-1 high-speed detector. The two theta scan used a Cu target at 35 kv and 45 ma. The diffraction patterns were taken in the range of 2° to 70°. The step size is 0.01794 degrees and the time/step is 0.1 second. Results are illustrated in FIG. 1, which shows the XRD patterns of 18.4% $CoMoS_x$+81.6% $ZrV_2$ and 49.2% $CoMoS_x$+50.8% $ZrV_2$ as well as the reference samples of $ZrV_2$ alloy and $ZrV_2H_{4.5}$ metal hydrides. There are no crystallized phases of CoMo and $ZrV_2$ sulfides detected by XRD. CoMo and $ZrV_2$ sulfide phases are either amorphous, or highly dispersed or in the states of fine crystallites. The two theta values of $ZrV_2H_{4.5}$ metal hydrides are lower than those of metal alloy of $ZrV_2$, which indicates monatomic hydrogen insertion into the lattices of $ZrV_2$, resulting in certain expansion of $ZrV_2$ unit cells. The unit cells of $ZrV_2$ in $CoMoS_x/ZrV_2$ are between those of the $ZrV_2$ alloy and the $ZrV_2H_{4.5}$ metal hydrides. This implies that some hydrogen was removed from $ZrV_2$ metal hydrides during the calcination in $N_2$ at 650° F. The higher loading of amorphous $CoMoS_x$ on $ZrV_2$ metal hydrides reduces the intensity of the characteristic diffraction peaks of $ZrV_2$ metal hydrides.

Example 3A

This example describes how the Group VI/Group VIII metal sulfides were deposited on the surfaces of the CAT 400 iMeH components to form exemplary catalysts of the invention. In this example, the CAT 400 formulation was $ZrV_2$ as described in Example 1; the Group VI/Group VIII metal sulfide is $NiMoS_x$.
Preparation of the $NiMoS_x/ZrV_2$ Catalyst (Labeled Herein as the "NiMoSx (Coated)/Hydride Catalyst")

$NiMoS_x/ZrV_2$ samples were prepared by mixing, grinding Ni and Mo thio salts with $ZrV_2$. The mixture was then calcined in nitrogen. Inside a nitrogen atmospheric glove box, appropriate amount of $ZrV_2$ metal hydrides were mixed with appropriate amounts of $(NH_4)_2Mo_3S_{13}$ (ammonium polythiomolybdate) and $Ni[(C_2H_5)_2NCS_2]_2$ (nickel diethyldithiocarbamate). The sample was placed in a nitrogen containing bag and pressed under 30 tons for 10 min. The pressed sample disks were broken into pieces. The chunks of the sample pieces are placed inside a tube furnace. The furnace was purged in $N_2$ for 2 hrs. The tube furnace was ramped from room temperature to 392° F. at rate of 10° F./min and held at 392° F. for 2 hrs. After holding, the furnace was ramped again from 392 to 650° F. at 10° F./min and held at 650° F. for 3 hrs. The reactor system was cooled off in nitrogen flow to room temperature. Catalyst samples with compositions of 0%, 50% and 100% by weight of $NiMoS_x$ on $ZrV_2$ iMeH were prepared.

Example 3B

In this example, a the Group VI/Group VIII metal sulfide catalyst, similar to as was prepared in Example 3A with the main exception that the interstitial metal hydride component (i.e., $ZrV_2$) was not included. The catalyst of this example was used as a base example to test the synergistic effects of a catalyst of invention as detailed in Example 6 herein.
Preparation of the $NiMoS_x$ Coated Catalyst (Labeled Herein as the "NiMoSx (Coated) Catalyst")

NiMoSx coated samples were prepared by mixing, grinding Ni and Mo thio salts. The mixture was then calcined in nitrogen. Inside a nitrogen atmospheric glove box, appropriate amount of $(NH_4)_2Mo_3S_{13}$ (ammonium polythiomolybdate) was mixed with $Ni[(C_2H_5)_2NCS_2]_2$ (nickel diethyldithiocarbamate). The sample was placed in a nitrogen containing bag and pressed under 30 tons for 10 min. The pressed sample disks were broken into pieces. The chunks of the sample pieces are placed inside a tube furnace. The furnace was purged in $N_2$ for 2 hrs. The tube furnace was ramped from room temperature to 392° F. at rate of 10° F./min and held at 392° F. for 2 hrs. After holding, the furnace was ramped again from 392 to 650° F. at 10° F./min and held at 650° F. for 3 hrs. The reactor system was cooled off in nitrogen flow to room temperature.

Example 4

The procedures of this example were used to measure the activities of the catalysts of the invention as made in Example 2 ($CoMoS_x/ZrV_2$) in the presence of model feeds.

HiP/HOSS, standing for High Pressure Reactors and Heated Orbital Shaker System, is a batch reactor unit used for catalyst activity evaluation. The catalyst samples were pretreated in nitrogen at 150° C. for 1 hr. The catalysts were then sulfided at two stages, i.e., 250° C. for 2 hrs, and 360° C. for another 2 hrs. 10% $H_2S$ balanced with $H_2$ was used for catalyst sulfiding. After sulfiding, the catalysts were cooled down to 25° C. under 10% $H_2S$ balanced with hydrogen flow and were purged with nitrogen for another 1.5 hrs before additions of the model feeds. Feeds with three model compounds were used for catalyst activity evaluations. These three model feeds are poly alpha olefins based (PAO, 6 centistokes) and spiked with 0.3% dibenzothiophene (DBT), 0.3% 4,6-diethyldibenzothiophene (DEDBT), and 1% 1n-dodecyl ($C_{12}$) naphthalene, respectively. The 60-250 mg of catalysts were loaded into HiP/HOSS, which is 0.5-2 VHSV equivalent. The catalytic evaluation tests were carried out at 280° C. with hydrogen partial pressure of 200 psig.

Figure 2:
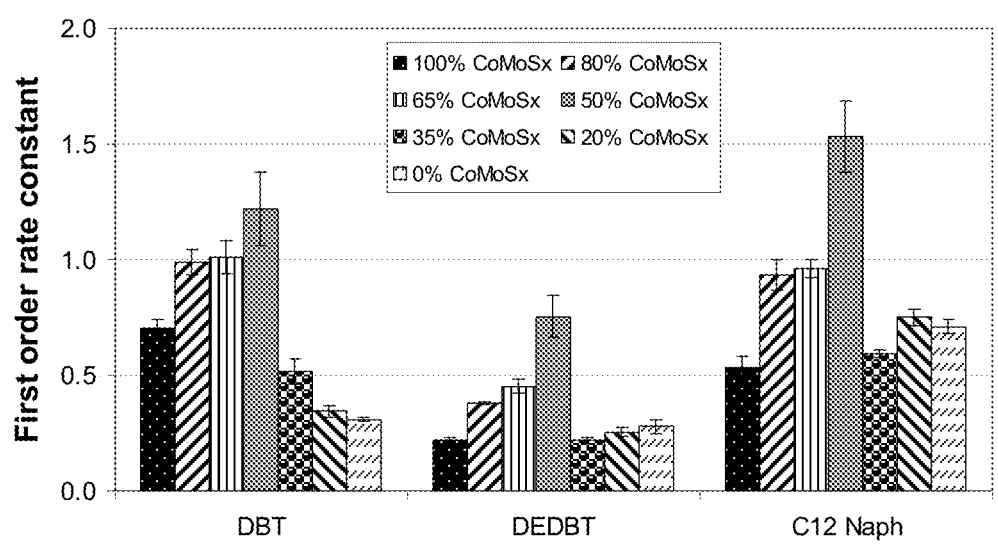
FIG. 2 is a graph depicting first order rate constants for conversion of dibenzothiophene (DBT), 4,6-diethyldibenzothiophene (DEDBT) and 1n-dodecylnaphthalene ($C_{12}$ naph) in model feeds, in the presence of $CoMoS_x/ZrV_2$ catalysts of the invention.

Results for the model feeds are illustrated in FIG. 2, which shows the first order rate constants for disappearance of DBT, DEDBT and $C_{12}$ naphthalene for the $CoMoS_x/ZrV_2$ samples. HiP results revealed that catalytic activity changes as a function of catalyst composition. The activity of $CoMoS_x/iMeH$ is generally much higher then the summation of $CoMoS_x$ and iMeH alone, which indicates the synergetic effect of $CoMoS_x/iMeH$. For the catalyst of 50% $CoMoS_x$/50% $ZrV_2$, the rate of monatomic hydrogen produced by iMeH may match the rate of hydrogen consumption on the $CoMoS_x$. It has the highest activity for dibenzothiophene (DBT), diethyldibenzothiophene (DEDBT), and $C_{12}$ naphthalene.

Example 5

This example describes how a bulk Group VI/Group VIII metal sulfide, $NiMoS_x$, was prepared. This material was used for comparative testing with a catalyst of the invention in Example 6.
Preparation of the Bulk Group VI/Group VIII Metal Sulfide, $NiMoS_x$ Catalyst (Labeled Herein as the "NiMoSx (Bulk) Catalyst")

1. Press 200 g total in 3 g portions of $(NH_4)_2Mo_3S_{13}$ into wafers (10 tons/3 minutes)
2. Load pressed material into furnace, then purge with nitrogen (room temperature, 1 L/min) for 30 minutes
3. Heat quickly to 400° C. (752° F.) under nitrogen (25° C./min or room temperature to 400° C. in 15 minutes)
4. Hold at 400° C. (752° F.) for 30 minutes
5. Allow unit to cool to room temperature (still under nitrogen)

6. Unload the $MoS_x$ in an inert atmosphere
7. Under an inert atmosphere combine the $MoS_x$ with 30 g of bis(1,5-cyclooctadiene) nickel(0) and 1 L of anhydrous THF and stir at room temperature for 24 hrs.
8. Filter the mixture and wash the $NiMoS_x$ with THF until the washes are colorless.
9. Dry the $NiMoS_x$ under vacuum and store in an inert atmosphere.

Example 6

This example illustrates the results of comparative activity assays for a 1) CAT 400 iMeH ($ZrV_2$) alone (labeled as "CAT 400 ($ZrV_2$)" in this example, and as prepared in Example 1 herein), 2) a catalyst of the invention ($NiMoS_x/ZrV_2$) (labeled as "NiMoSx (coated)/hydride catalyst" in this example, and as prepared in Example 3A herein), 3) a Group VI/Group VIII thiol-derived metal sulfide ($NiMoS_x$) alone (labeled as "NiMoSx (coated) catalyst" in this example, and as prepared in Example 3B herein), 4) a Group VI/Group VIII bulk metal sulfide ($NiMoS_x$) alone (labeled as "NiMoSx (bulk) catalyst" in this example, and as prepared in Example 5 herein), and 5) a formulation in which separate particles of $ZrV_2$ (CAT 400, from Example 1) and $NiMoS_x$ (from Example 5) where the catalyst was prepared by combining the separate particles and pressing them (i.e., physical pressure only, no binder was used) (labeled as "NiMoSx (bulk)/hydride catalyst" in this example).

The NiMoSx (coated)/hydride ($NiMoS_x/ZrV_2$) catalyst of the invention used in this example was prepared as described in Example 3A, where the weight ratio of the two components is 50:50. Testing of activities of the catalysts of this example in the presence of model feeds were carried out in a similar manner as the procedures described in Example 4 for the $CoMoS_x/ZrV_2$ catalysts.

Figure 3:
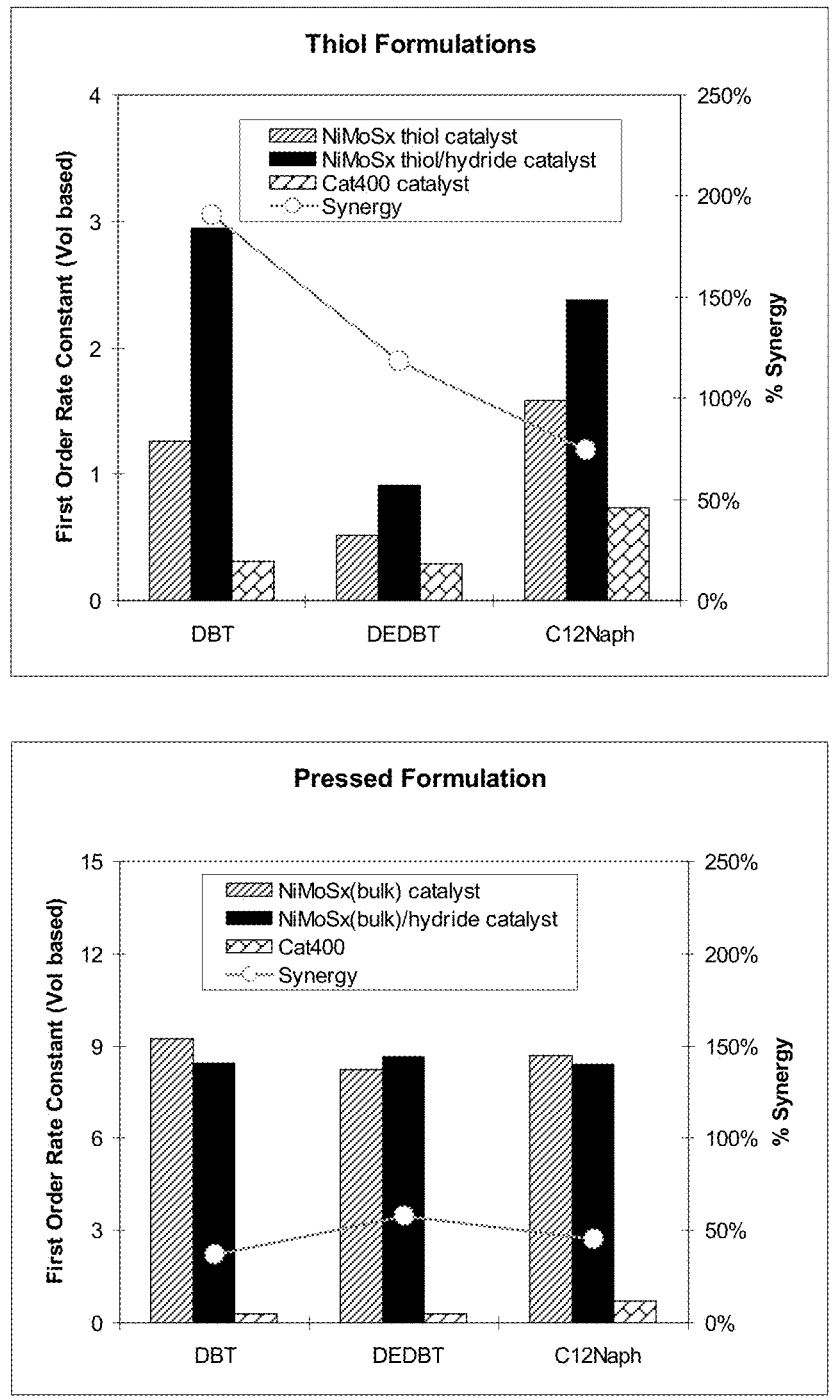
FIG. 3 depicts graphs of the first order rate constants for the conversion of dibenzothiophene (DBT), 4,6-diethyldibenzothiophene (DEDBT) and 1n-dodecylnaphthalene ($C_{12}$ naph) in model feeds, in the presence of $NiMoS_x/ZrV_2$ catalysts of the invention (top graph), compared to the first order rate constants in the presence of $NiMoS_x$ alone, $ZrV_2$ alone, and a pressed formulation of $NiMoS_x$ and $ZrV_2$ (bottom graph).

Results are illustrated in Table 2 and in FIG. 3. In the data of this example, any value for "Synergy" that is greater than 0% shows a synergistic effect due to the combination of components as manufactured per the techniques indicated over the simple addition of the activities of the separate components.

TABLE 2

First order rate constants for the disappearance of DBT, DEDBT and $C_{12}$ naphthalene in model feeds.

|  | DBT | | DEDBT | | C12 Naph | |
| --- | --- | --- | --- | --- | --- | --- |
|  | k | +/− | k | +/− | k | +/− |
| NiMoSx (coated) catalyst | 1.26 | 0.05 | 0.51 | 0.02 | 1.58 | 0.22 |
| CAT 400 (ZrV2) | 0.31 |  | 0.29 |  | 0.73 |  |
| NiMoSx (coated)/hydride (50/50) | 2.94 | 0.07 | 0.91 | 0.07 | 2.37 | 0.23 |
| Synergy | 191% |  | 118% |  | 74% |  |
| NiMoSx (bulk) | 9.24 | 0.12 | 8.23 | 0.14 | 8.68 | 0.23 |
| CAT 400 (ZrV2) | 0.31 |  | 0.29 |  | 0.73 |  |
| NiMoSx (bulk)/hydride (50/50) | 8.44 | 0.04 | 8.64 | 0.01 | 8.39 | 0.01 |
| Synergy | 37% |  | 58% |  | 45% |  |

As can be seen in Table 2 and corresponding FIG. 3, the "NiMoSx (bulk)/hydride" catalyst as prepared by the "bulk" method (or simply pressing the catalyst components together as may be taught by the prior art) does show that there is a synergistic effect in combining the GrVI/GrVIII/Sx catalyst with the interstitial metal hydride (CAT 400) component. However, as can also be seen in Table 2 and corresponding FIG. 3, in a catalyst embodying the present invention (i.e., the NiMoSx (coated)/hydride" catalyst), significant and unexpected improvements in the synergistic effects in activity improvements (i.e., first order rate constants) are shown in all categories tested.

Synergy quantification is a two step calculation. First the "predicted" rate constant is calculated. This calculation takes the measured rate constant of the individual components and the composite catalyst's composition and determines what the rate constant would be if there were no interactions between the components.

For example, viewing the data in Table 2, the NiMoSx (coated) catalyst has a (volumetric) rate constant for DBT of 1.26±0.05 and CAT400 catalyst has a DBT rate constant of 0.31±0.03. The 50/50 (by weight) NiMoSx (coated)/hydride catalyst is 73.5% NiMoSx and 26.5 hydride (CAT 400) by volume, thus the predicted rate constant for that material is:

0.735*1.26+0.265*0.31=1.01

Synergy is effectively how much more active the composite material is over what would be expected from its components. The synergy is calculated by taking the difference between the measured and predicted values and dividing it by the predicted value and multiplying it by 100. Thus synergy would be 0% if the measured and predicted values were the same. The measured rate constant of the 50/50 by weight NiMoSx thiol/hydride was 2.94±0.07. Thus the synergy of this catalyst is:

(2.94−1.01)/(1.01)*100=191%

Preferably the catalysts of the present invention have synergies values for DBT conversion, DEDBT conversion, or C12 Naphthalene conversion of at least, 70%, more preferably at least 100%, and even more preferably at least 150%, All patents, publications and references cited herein are hereby fully incorporated by reference. In case of conflict between the present disclosure and incorporated patents, publications and references, the present disclosure should control.

What is claimed is:

1. A process for upgrading a hydrocarbon feedstream, comprising contacting a hydrocarbon feedstream with a catalyst comprising an interstitial metal hydride having a surface and a Group VI/Group VIII metal sulfide coated on the surface of the interstitial metal hydride, in the presence of hydrogen to yield an upgraded hydrocarbon product stream.

2. The process of claim 1, wherein the process is performed in the presence of a hydrogen-rich gas containing at least 50 mol % hydrogen.

3. The process of claim 1, wherein the hydrocarbon feedstream is a heavy hydrocarbon feedstream with an API gravity of less than 20 and a sulfur content of at least 1 wt % sulfur.

4. The process of claim 1, wherein the hydrocarbon feedstream comprises a biofuel.

5. The process of claim 1, wherein the process is a hydroprocessing process selected from hydrogenation, hydrocracking, hydrodesulfurization, hydrodenitrogenation, hydrodemetalization, and catalytic hydrodewaxing processes.

6. The process of claim 1, wherein the Group VI metal is selected from Mo and W; the Group VIII metal is selected from Fe, Co, Ni, Pd, and Pt; and wherein the interstitial metal hydride and the Group VI/Group VIII metal sulfide are present in a ratio of about 20:80 by weight to about 80:20 by weight.

* * * * *